(12) United States Patent
Richter et al.

(10) Patent No.: US 9,623,199 B2
(45) Date of Patent: Apr. 18, 2017

(54) INJECTION DEVICE

(71) Applicant: Sanofi-Aventis Deutschland GmbH, Frankfurt am Main (DE)

(72) Inventors: Frank Richter, Bad Tolz (DE); Ross Macarthur, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 0 days.

(21) Appl. No.: 14/419,457

(22) PCT Filed: Aug. 12, 2013

(86) PCT No.: PCT/EP2013/066772
§ 371 (c)(1),
(2) Date: Feb. 3, 2015

(87) PCT Pub. No.: WO2014/026935
PCT Pub. Date: Feb. 20, 2014

(65) Prior Publication Data
US 2015/0190590 A1    Jul. 9, 2015

(30) Foreign Application Priority Data

Aug. 14, 2012  (EP) .................................... 12180357

(51) Int. Cl.
*A61M 5/50*    (2006.01)
*A61M 5/20*    (2006.01)
(Continued)

(52) U.S. Cl.
CPC ............ *A61M 5/5086* (2013.01); *A61M 5/20* (2013.01); *A61M 5/3157* (2013.01);
(Continued)

(58) Field of Classification Search
CPC ............ A61M 5/31526; A61M 5/3157; A61M 5/322; A61M 5/326; A61M 2205/518;
(Continued)

(56) References Cited

U.S. PATENT DOCUMENTS 5,391,157 A * 2/1995 Harris ................ A61M 5/31511
604/208
2005/0027255 A1 * 2/2005 Lavi .................... A61M 5/2033
604/135
(Continued)

FOREIGN PATENT DOCUMENTS

EP          0730876 B1    6/2000
WO     2005113039 A1    12/2005
(Continued)

*Primary Examiner* — Laura Bouchelle
*Assistant Examiner* — Justin L Zamory
(74) *Attorney, Agent, or Firm* — Fish & Richardson P.C.

(57) ABSTRACT

The invention refers to an injection device comprising a delivery mechanism for injection of a medicament, preferably through a needle, and an end of dose mechanism comprising a feedback element, wherein the end of dose mechanism is operable to be activated at a position at which the delivery mechanism reaches the end of the dose and the end of dose mechanism is further operable to force the feedback element to move into a feedback direction which is opposite or parallel to the activation direction of a release button and/or into the longitudinal direction, wherein the activation direction is preferably a longitudinal direction of the device.

20 Claims, 5 Drawing Sheets

(51) Int. Cl.
  *A61M 5/32*    (2006.01)
  *A61M 5/315*    (2006.01)
(52) U.S. Cl.
  CPC ............ *A61M 5/322* (2013.01); *A61M 5/326* (2013.01); *A61M 2205/581* (2013.01); *A61M 2205/582* (2013.01); *A61M 2205/583* (2013.01); *A61M 2205/584* (2013.01)
(58) Field of Classification Search
  CPC ...... A61M 2205/582; A61M 2205/583; A61M 2205/584
  See application file for complete search history.

(56) References Cited

U.S. PATENT DOCUMENTS

| | | | |
|---|---|---|---|
| 2008/0243087 A1* | 10/2008 | Enggaard | A61M 5/31553 604/208 |
| 2009/0012479 A1* | 1/2009 | Moller | A61M 5/3155 604/211 |
| 2009/0318865 A1* | 12/2009 | Moller | A61M 5/31553 604/135 |
| 2010/0137798 A1 | 6/2010 | Streit et al. | |

FOREIGN PATENT DOCUMENTS

| | | | |
|---|---|---|---|
| WO | 2006079481 A1 | 8/2006 | |
| WO | 2011123024 A1 | 10/2011 | |
| WO | 2012030277 A1 | 3/2012 | |

* cited by examiner

INJECTION DEVICE

CROSS REFERENCE TO RELATED APPLICATIONS

The present application is a U.S. National Phase Application pursuant to 35 U.S.C. §371 of International Application No. PCT/EP2013/066772 filed Aug. 13, 2013, which claims priority to European Patent Application No. 12180357.1 filed Aug. 14, 2012. The entire disclosure contents of these applications are herewith incorporated by reference into the present application.

FIELD OF INVENTION

The present invention is directed to an injection device comprising a delivery mechanism for injection of a medicament, preferably through a needle.

BACKGROUND

The invention particularly refers to autoinjectors which are medical devices designed to deliver a single dose of a particular medicament. Autoinjectors are easy to use and are intended for self-administration by patients, or for administration by untrained personnel. However, the present invention is not limited to this type of injection devices but is also applicable to syringes and pens which enable accurate and controlled dosage prior injection and which are reusable or disposable.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Today's known autoinjectors keep the needle tip shielded prior to injection and also comprise a passive safety mechanism to prevent accidental firing (injection). Just by pressing a release button, the syringe needle is automatically driven out and the medicament is delivered.

One of the problems using such autoinjectors is that the often the full dose is not delivered because of several reasons. However, it is necessary to administer the full dose in order to reach full effectiveness of the medicament within the treated body of human being or animal. Hence, for easier recognition of full delivery, some autoinjectors available at the market have a visual indication to confirm that the full dose was spent.

Document EP 0 730 876 B1 discloses a medical dispensing device comprising an end-of-dose click arrangement which creates an audible "click" sound thereby providing an audible confirmation that the entire dosage has been injected. This sound is produced by an edge of a flexible finger moving past a housing edge and into a groove.

Further, from document WO 2006/079481 A1 an injection device with a dose delivering mechanism and an end of dose feedback mechanism is known. Therein a first and a second part of an injection device are adapted to perform a relative rotational movement with respect to each other during injection of a dose. The relative rotational movement causes at least two parts of the injection device to abut or engage, the abutment or engagement causing a non-visual feedback signal to be generated. This may be generated, e.g., by a change in rotational velocity of at least one part of the injection device, for example by changing a pitch of a threaded portion, or by engaging a non-rotating part and a rotating part thereby causing the non-rotating part to start rotating.

The disadvantage of the above state of the art end-of-dose indications is that they may be overheard or can only hardly be recognized in a tactile manner. A single click sound in a loud environment is easily overheard. A change of velocity of a rotational movement may be not as clear and distinct enough that a user clearly feels a tactile signal.

SUMMARY

It is therefore an object of the present invention to provide an injection device being capable of very clearly and distinctly indicate in a tactile manner to a user that a full dose was injected.

This is obtained by an injection device as defined in claim 1.

The main aspect of the invention is that the device comprises an end of dose mechanism with a feedback element, wherein the end of dose mechanism is operable to be activated at a position at which the delivery mechanism reaches the end of dose and the end of dose mechanism is further operable to force the feedback element to move into a feedback direction which is opposite or parallel to the activation direction of a release button and/or parallel to a longitudinal direction, wherein the feedback direction is preferably a longitudinal direction of the device. Herein, the activation direction is the direction into which the release button is pressed in order to activate the injection of the medicament.

The advantage of the inventive injection device consists therein that the movement of the feedback element at the end of the dose is opposite or parallel to the activation direction or in longitudinal direction. Therein the movement of the feedback element does not comprise a rotational movement but only a lengthwise movement which is parallel or opposite to the activation direction or parallel to the longitudinal direction. The inventors have found that if the movement of a feedback element goes in one of these directions it could be easily felt by the user and therefore easily recognized because the displacement of the feedback element causes a backstroke, kickback or repulsion force. The activation direction may be parallel to the longitudinal direction of the device which is parallel to the longitudinal axis of the device. Alternatively, the activation direction may be perpendicular to the longitudinal direction or any other direction.

Further it is preferred if the feedback element is separate from the elements within the housing of the injection device which effect the injection of the medicament like a lead screw or a gear drive. In a preferred embodiment the feedback element is an element with is in direct contact with the skin of the patient or the person administering the medicament, for example the health care practitioner. Then, the movement of the feedback element is directly felt by the patient or the user.

In an embodiment of the invention, the injection device may be realized in the following versions: In case that the feedback element comprises the release button, preferably its proximal end face, the feedback element is forced to move into the feedback direction which is parallel or opposite the activation direction, wherein the activation direction is preferably parallel to the longitudinal direction of the device. Alternatively or additionally, if the or another feedback element comprises the housing or the needle cover, respectively, preferably, the distal end face of the housing or the needle cover, respectively, the feedback element is forced to move into the feedback direction which is the distal longitudinal direction of the device.

The inventive device may be used for veterinary applications, pediatric applications or applications designed for older users because the end of dose mechanism is so strong that even younger or older people feel the backstroke well. By the invention, a tactile cognitive feedback at the end of dose is provided which is much stronger than the one provided by the above described state of the art feedback mechanism comprising rotating elements, e.g., a change in rotational velocity.

The cognitive feedback avoids errors during application of the device, in particular underdose is avoided which happens when the injector is removed too early.

Further, the medicament dose may be precisely dimensioned in advance because the end of dose mechanism stops the injection of further medicament at the time point or the position of the elements of the injection device at which the end of dose is reached. Hence, no medicament drips off the injection device and skin irritations (e.g. by Enoxaparin) are avoided after removal of the injection device.

According to an embodiment, the end of dose mechanism of the new inventive injection device may comprise a pre-loaded or pre-loadable spring. The spring is a member of the end of dose mechanism and is activated at a position of a component of delivery mechanism at which the injection device reaches the end of dose during injection of the medicament and thereby freed or resiled to force the feedback element to move into one of the directions described above.

The cognitive feedback is particularly strong in the case in which the end of dose mechanism is operable to abruptly force the feedback element into the above described feedback direction.

An easy and cost efficient way to realize an inventive injection device is provided if the device comprises a lead screw operable to rotate relative to a nut during injection. Preferably such lead screw comprises a plunger at its distal end which drives
the medicament out of a cartridge. A lead screw is particularly used in an inventive injection device in which user-defined dose may be dialed for injection.

In particular, if a lead screw is used in the injection device in an embodiment the delivery mechanism may comprise a radial element, for example a rod with a longitudinal direction accommodated radially with regard to the device, which preferably projects from the lead screw. The radial element is operable to pass a radial opening, preferably of a plate, at the end of dose in order to activate the end of dose mechanism. Alternatively, the delivery mechanism may comprise two engaged elements operable to disengage them at the end of dose in order to activate the end of dose mechanism.

A further enhancement of the tactile feedback can be reached in an embodiment in which the end of dose mechanism comprises ratchet means. Preferably, during the displacement of the feedback element the ratchet means are overridden by a resilient finger simultaneously so that the user feels a bumpy or rugged movement within the above described feedback direction.

In a preferred embodiment, the end of dose mechanism comprises a stop member which abruptly stops the movement of the feedback element. The stop member may further produce a sound feedback, preferably by an abutment of an element of the device against the stop member.

In a further embodiment the end of dose mechanism may provide an audible signal like a "click" sound. Alternatively or additionally the end of dose mechanism may produce a visible signal, e.g., it may show flashing light signal, for example produced by an LED, or it may show a color change or the like.

In another embodiment, the end of dose mechanism may be operable to enclose or retract the needle, so that the same mechanism on one hand signalizes the end of dose and on the other hand protects the needle. In this embodiment, the inventive injection device advantageously provides a safety needle mechanism and is therefore also usable in hospitals.

Preferably, the inventive injection device comprises a cartridge containing a medicament which is injected preferably through a needle during injection. The injection is controlled by the operation of an release button which is pressed in the activation direction which is preferably a longitudinal direction of the device in order to inject the medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28)
human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone.

The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17.ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The person skilled in the art understands that the present invention is not restricted to the explained possibilities.

The above-mentioned advantages as well as other advantages of various aspects of the present invention will become apparent to those of ordinary skill in the art by reading the following detailed description with the explanation of the accompanying drawings.

BRIEF DESCRIPTION OF THE DRAWINGS

Exemplary embodiments of the present invention are described herein with reference to schematic drawings in which.

DETAILED DESCRIPTION

The figures are schematic and simplified for clarity and they only show details which are essential to the understanding of the invention while other details are left out. Further, the term "distal end" in the accompanying drawings is meant to refer to the end of the injection device carrying an injection needle whereas the term "proximal end" is meant to refer to the opposite end pointing away from the injection needle.

In the following, the description of preferred embodiments refers to autoinjectors which do not have the possibility to dial a user-defined dose. Rather, the autoinjectors contain a pre-defined dose for example for an adult human being or an adult animal. However, the explained features can also be applied to a syringe or autoinjector which is enabled to dial a user-defined dose prior injection. Further, the invention can be used in injection devices which are reusable or disposable.

Figure 1:
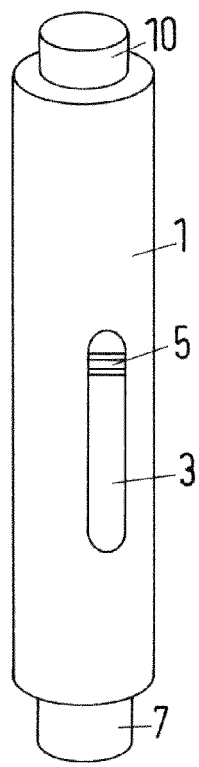
FIG. 1 illustrates a perspective view of an inventive injection device prior injection, FIG. 2 a perspective view of a first embodiment of an inventive injection device prior (a)) and during (b)) injection as well as (c)) at the end of dose, FIG. 3 a force-displacement-diagram for the inventive injection device according to FIG. 2, FIG. 4 a perspective view of a second embodiment of an inventive injection device at the end of dose, FIG. 5 a perspective view of a third embodiment of an inventive injection device prior (a)) and during (b)) injection as well as (c)) at the end of dose, FIG. 6 a perspective view of a fourth embodiment of an inventive injection device at the end of dose, FIG. 7 a cross section of the inventive injection device according to FIG. 2 prior to (a)) and at the end of dose (b)), FIG. 8 a cross section of the inventive injection device according to FIG. 5 prior to (a)) and at the end of dose (b)), FIG. 9 a cross section of a part of the end of dose mechanism of a modification of the fourth embodiment of an inventive injection device, FIG. 10 a force-displacement-diagram for the inventive injection device according to FIG. 9, and FIG. 11 a perspective view of a part of the delivery mechanism of the fourth embodiment of the inventive injection device.

FIG. 1 shows the principle construction of an inventive autoinjector. The autoinjector comprises a medicament 3 contained within a cartridge. The cartridge is accommodated within a housing 1. At the distal end, the autoinjector comprises a needle shield 7 which encloses and protects the needle accommodated therein and provides needle safety after injection. Alternatively the autoinjector may comprise a needle retraction unit which retracts the needle after injection of the full dose automatically. During administration the medicament 3 is forced by a plunger 5 into distal direction for injection through the needle. At the proximal end of the autoinjector, an release button 10 is accommodated which activates a delivery mechanism for injection of the pre-defined dose of medicament 3. The release button 10 is operable to be pressed by the user e.g. into distal longitudinal direction for activation.

Figure 2:
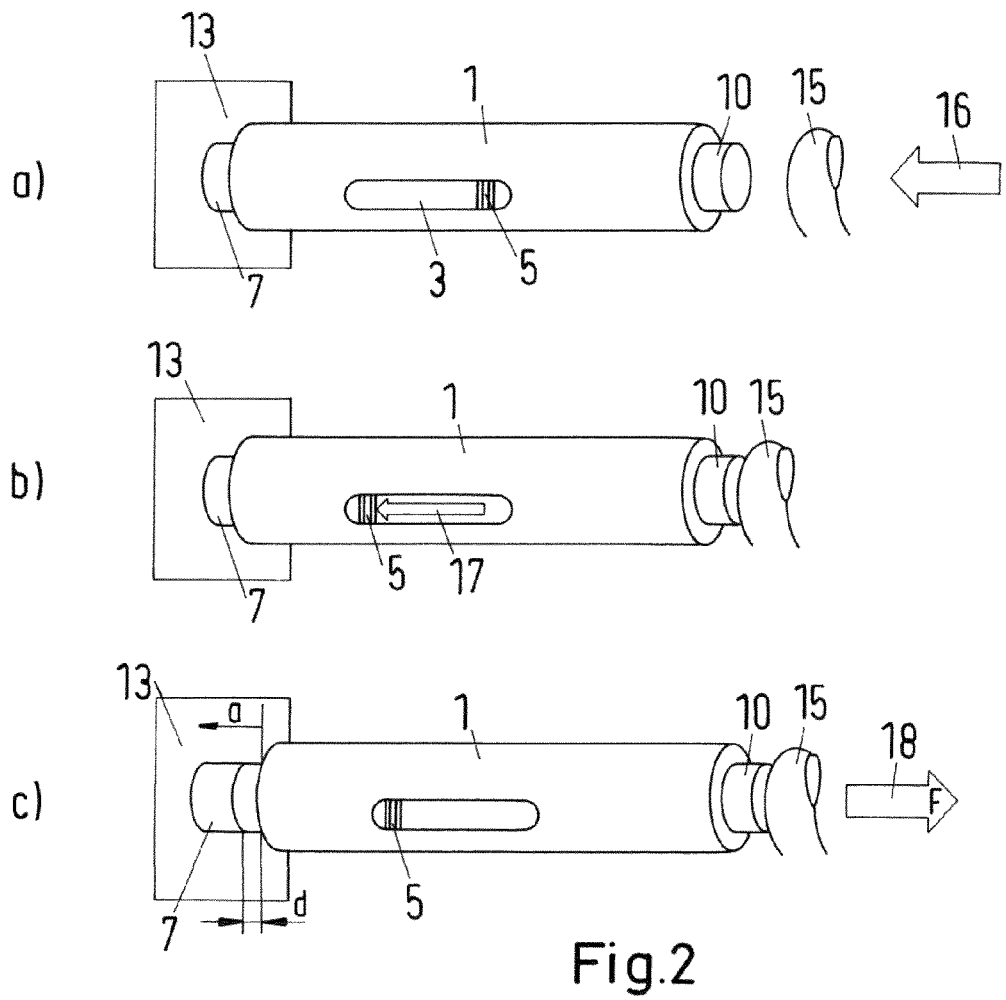

In FIG. 2, the injection of a pre-defined dose of medicament is explained with regard to a first embodiment of an inventive autoinjector. With regard to this and the following embodiments, it shall be pointed out that the injection is activated by pressing the release button by a user which may be the patient his/herself or another person.

In the first step (shown in FIG. 2a)), the autoinjector is placed with its needle shield 7 at the skin 13 of a human being or animal to be treated. Now, the user is going to inject the pre-defined dose of the medicament 3 and therefore presses the release button 10 with its finger 15 (see FIG. 2b)) into the distal direction (activation direction, depicted in FIG. 2a) by arrow 16). By pressing the release button 10 with finger 15 into the longitudinal distal direction, the delivery mechanism is activated which moves a plunger 15 into distal direction (this direction is marked with arrow 17) so that the medicament 3 is administrated through the needle (not shown). After the full pre-defined dose is administered, the end of dose is reached. Now the delivery mechanism releases the end of dose mechanism realized within the autoinjector. This can be achieved by the position of an internal component of the autoinjector reaching the end of dose point. One example of the activation of the end of dose mechanism is described with regard to FIG. 11 below.

In the embodiment shown in FIG. 2, a feedback element of the end of dose mechanism comprises the needle shield 7. If once the end of dose mechanism is activated as shown in FIG. 2c), the needle shield 7 is forced to move into distal direction (feedback direction, see arrow a), for example by release of a pre-compressed spring. By this, the needle shield 7 is moved out of (or is elongated from) the distal end of the housing 1 of the autoinjector by a distance d. At the same time, the needle automatically is withdrawn from the skin 13 and enclosed by the by distance d elongated needle shield 7. This distal force of the autoinjector at the end of dose is felt like an impact and is therefore easily recognized by the patient at his/her skin. The subsequent backward movement of the device the user easily recognizes as a backstroke at his/her finger 15. By this, the user and the patient (if not the same person) know that the end of dose is reached and the user removes the autoinjector from skin 13.

Figure 3:
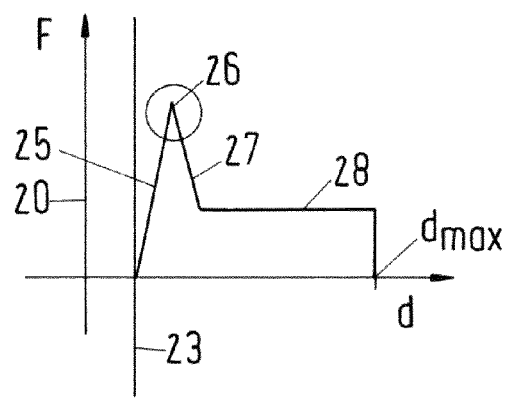

The behaviour of the inventive autoinjector is schematically depicted in the force-distance-diagram 20 of FIG. 3 wherein the cognitive force applied to the skin 13 into longitudinal distal direction (opposite to the direction depicted by arrow 18) is shown as a function of the distance d by which the needle shield 7 is extracted from the end of housing 1 of the autoinjector. At point 23 and a distance d of zero, the end of dose is reached and the end of dose mechanism is activated. Now the force F increases (see flank 25) driven by the end of dose mechanism until it reaches a maximum 26. Then, the force F slightly decreases (see flank 27) and reaches a plateau 28. If the needle shield 7 reaches a maximum elongation and hence a maximum distance $d_{max}$ the force F decreases until it reaches zero. In case the needle shield 7 is forced abruptly flank 25 is very steep.

Figure 4:
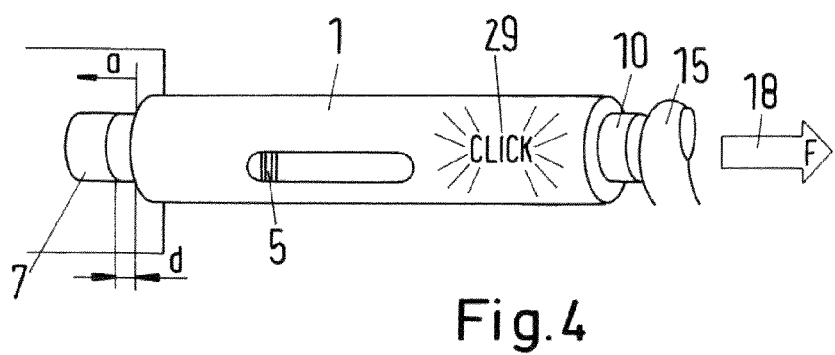

As shown in FIG. 4, the activation of the end of dose mechanism may be accompanied by an audible signal, for example a "click" sound (see reference no. 29).

Alternatively or additionally, the audible end of dose signal may be accompanied by a visual signal (not shown), e.g. by a flashing LED, a color change or the like.

Figure 5:
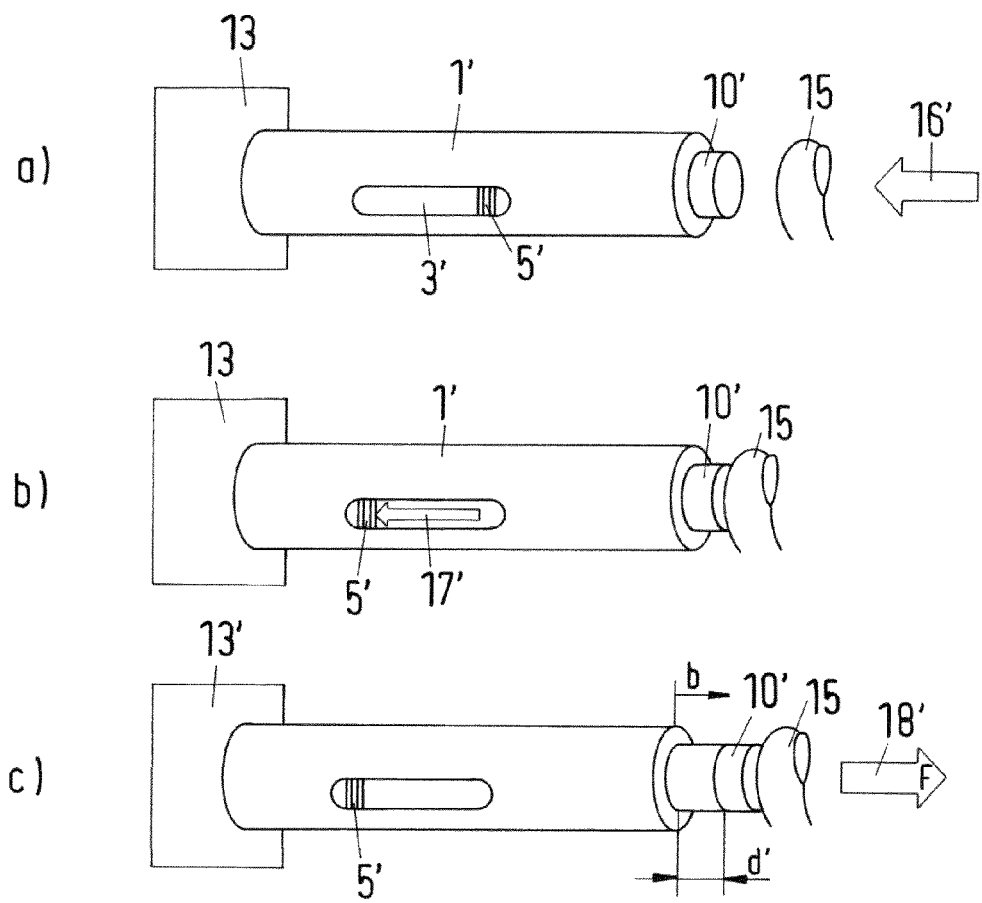

FIG. 5 shows another embodiment of an inventive autoinjector. Analogous to the method described with regard to FIGS. 2a) and b) in the first step the autoinjector is placed at skin 13 with its distal end of the housing 1'. Then, pressing of release button 10' by the user's finger 15 into the activation direction (see arrow 16') activates the delivery mechanism of the autoinjector and the plunger 5' drives the medicament 3' (see arrow 17') through the needle (not shown) and injects it into the treated person or animal.

If the end of dose is reached, the end of dose mechanism is activated and drives the release button 10' into proximal direction (feedback direction, see arrow b) out of the housing 1' by a distance d' and thereby applies a cognitive force to the finger 15 of the user into proximal longitudinal direction (see arrow 18') as a tactile signal. With regard to this embodiment the distance-force-diagram of FIG. 3 applies with the difference that instead of the distance d the distance d' of the elongation of the release button 10' from the housing 1' is shown.

Figure 6:
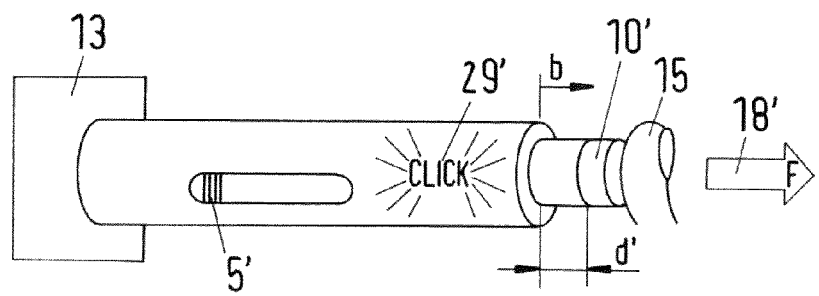

Analogues to the embodiment described with regard to FIGS. 2 and 4, the tactile signal of this embodiment may be combined with a visual and/or audible end of dose signal as well (see FIG. 6, reference sign 29').

Figure 7:
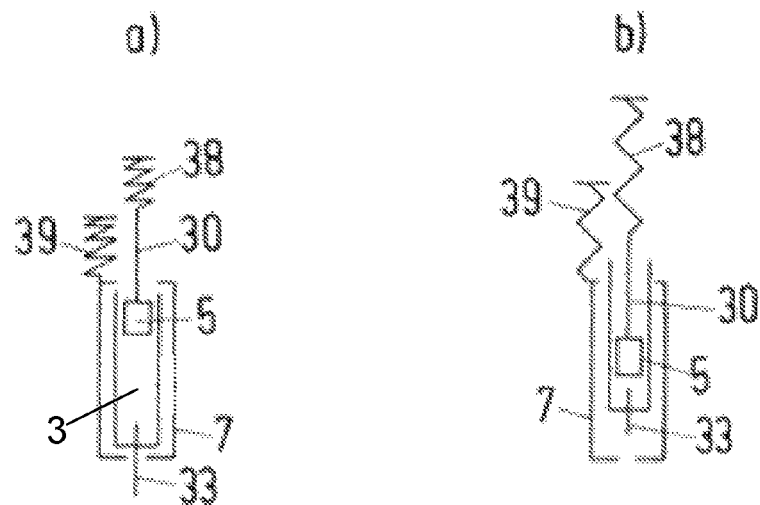
Figure 8:
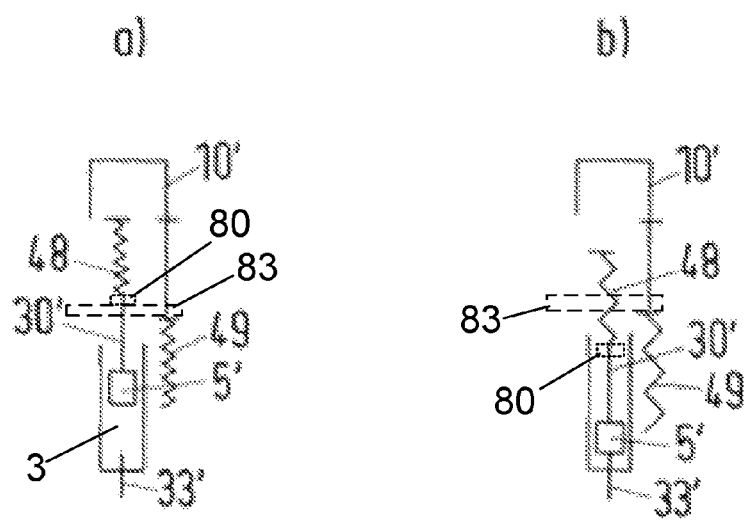

With regard to FIGS. 7 and 8, two possibilities of realization of an end of dose mechanism driving the needle shield 7 or dose button 10' of an autoinjector with lead screw 30, 30' as depicted in FIG. 2 or 5 are explained, respectively.

The inventive autoinjector comprises a delivery mechanism with a first spring 38 which is pre-loaded and drives the lead screw 30 with plunger 5 in distal direction in order to administer the medicament 3. FIG. 7a) shows the injection device during injection. If the end of dose is reached (see FIG. 7b)) a second spring 39, being pre-loaded as well is activated so that it drives needle shield 7 into distal direction and encloses needle 33. Automatically the needle 33 is retracted from skin 13.

During dose administration (see FIG. 8a)) of the embodiment as shown in FIG. 5 a pre-loaded first spring 48 drives a lead screw 30' with a plunger 5' into distal direction. If the end of dose is reached (see FIG. 8b)), a second pre-loaded spring 49 is activated to drive the release button 10' into proximal direction to provide a cognitive force to the finger 15 of the user. During the active time of the end of dose mechanism the needle 33' keeps inserted into the skin 13 of the treated person or animal. It is withdrawn from the skin 13 after the end of dose mechanism is finished during removal of the autoinjector. At the same time either a needle shield (not shown) may cover the needle or a needle retraction unit (not shown) retracts the needle into the housing 1' of the inventive device.

Figure 9:
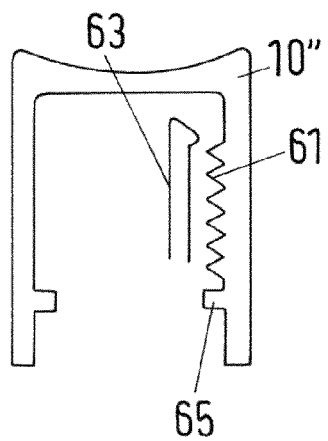

FIG. 9 shows an end of dose mechanism of the embodiment of the autoinjector as depicted in FIG. 6 which may be realized as a modification of the mechanism shown in FIG. 5. The end of dose mechanism provides ratchet means 61 at the inner surface of release button 10". A flexible finger 63 overrides ratchet means 61 during displacement of the release button 10" into proximal direction producing "click" sound. Finally, if the maximum displacement of the release button 10" is reached the edge of finger 63 abuts to a radial projection 65 which projects from the release button 10" into its inner volume.

Figure 10:
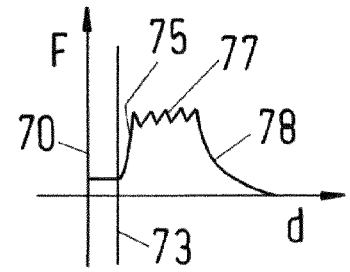

By this modified embodiment a different cognitive output is realized as depicted in FIG. 10 by the force-displacement-diagram 70. It is shown that the force curve comprises a first flank 71 at which the force F increases if the end of dose is reached at point 73. Then, a plateau 77 is reached where finger 63 overrides ratchet 61 and the user feels a bucking or bumpy force which is easy to recognize. If the end of the displacement of the release button 10" is reached force F decreases to zero at flank 78.

Figure 11:
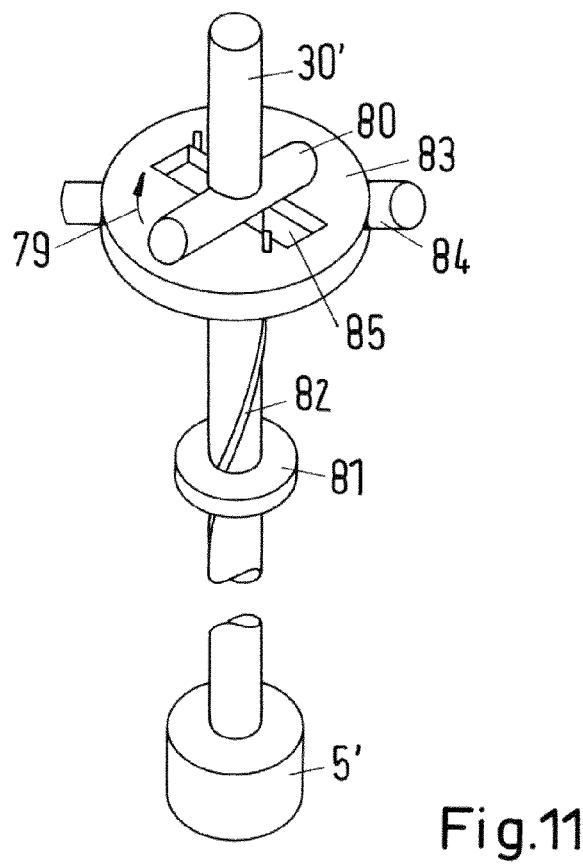

FIG. 11 depicts an easy to realize possibility to activate the end of dose mechanism. It is explained with regard to the embodiment of an autoinjector which was discussed with regard to FIGS. 6 and 8 above. During administration lead screw 30' rotates (see arrow 79) using thread 82 on the outer surface on the lead screw 30 relative to nut 81 until it reaches a stop element (peg). In particular the rotation of lead screw 30' is stopped by a not-shown projection on the inner diameter of nut 81. At this position a radially projecting rod 80 of lead screw 30' is aligned with a respective through hole 85 of a plate 83 accommodated by pins 84 within the housing 1 of the autoinjector. By this the plate 83 preloaded by second spring 49 is freed and able to drive into proximal direction in order to move the release button 10' into proximal longitudinal direction (feedback direction) as explained above.

Alternatively, plate 83 may rotate with respect to a non-rotatable lead screw 30' which is thereby moved into distal direction. In this case the plate 83 may comprise a helical groove which matches with the thread 83 of lead screw 30'.

The inventive autoinjector provides a cognitive feedback at the end of dose so that a user can easily feel that the end of dose is reached. The main aspect of the invention is that a tactile feedback is provided wherein the cognitive force acts into activation direction or opposite to it or into distal longitudinal direction. The tactile feedback avoids errors during use of the injection device so that underdosing is prevented.

The invention claimed is:

1. An injection device comprising:
   a delivery mechanism for injection of a medicament through a needle, the delivery mechanism comprising a radial element and a lead screw, the lead screw rotatable about a longitudinal axis of the injection device, and the radial element extending radially from the lead screw, and
   an end of dose mechanism comprising a feedback element and a radial opening extending radially from the longitudinal axis of the injection device,
   wherein the radial element of the delivery mechanism is operable to move along the longitudinal axis of the injection device to pass the radial opening of the end of dose mechanism to activate the end of dose mechanism when the delivery mechanism reaches an end of dose,
   wherein the end of dose mechanism is configured to move the feedback element in a feedback direction along the longitudinal axis of the injection device when the end of dose mechanism is activated, the feedback direction being along or opposite to an activation direction of a release button.

2. The injection device according to claim 1, wherein the feedback element comprises the release button and the feedback direction is opposite to the activation direction.

3. The injection device according to claim 1, wherein the end of dose mechanism comprises a spring that forces the feedback element to move when the end of dose mechanism is activated.

4. The injection device according to claim 1, wherein the end of dose mechanism is operable to abruptly force the feedback element into the feedback direction.

5. The injection device according to claim 1, wherein the lead screw is operable to rotate relative to a nut during the injection of the medicament.

6. The injection device according to claim 1, wherein the delivery mechanism comprises two engaged elements operable to disengage at the end of dose in order to activate the end of dose mechanism.

7. The injection device according to claim 1, wherein the end of dose mechanism comprises a ratchet mechanism positioned at an inner surface of the release button to generate an audible signal when the end of dose mechanism is activated.

8. The injection device according to claim 1, wherein the end of dose mechanism comprises a stop member configured to stop movement of the delivery mechanism when the delivery mechanism reaches the end of dose.

9. The injection device according to claim 1, wherein the end of dose mechanism generates an audible signal when the end of dose mechanism is activated.

10. The injection device according to claim 1, wherein the end of dose mechanism generates a visible signal when the end of dose mechanism is activated.

11. The injection device according to claim 1, wherein the end of dose mechanism is operable to retract the needle when the end of dose mechanism is activated.

12. The injection device of claim 1, further comprising:
    a housing; and
    a needle shield movable relative to the housing,
    wherein the feedback element comprises the needle shield of the injection device and the feedback direction corresponds to a distal direction along the longitudinal axis of the injection device.

13. The injection device of claim 1, wherein:
    the release button is disposed on a proximal end of a housing of the injection device,
    the feedback element comprises the release button,
    the activation direction corresponds to a distal direction along the longitudinal axis of the injection device, and
    the feedback direction corresponds to a proximal direction along the longitudinal axis of the injection device.

14. The injection device of claim 13, wherein the end of dose mechanism comprises:
    a plate defining the radial opening, and
    a spring configured to drive the plate in the proximal direction along the longitudinal axis of the injection device,
    wherein, when the end of dose mechanism is activated, the spring drives the plate past the radial element of the delivery mechanism in the proximal direction to move the release button in the proximal direction.

15. The injection device of claim 1, wherein the delivery mechanism is activated when the release button is moved in the activation direction.

16. The injection device of claim 15, further comprising a plunger coupled to the delivery mechanism and movable along the longitudinal axis of the injection device, the plunger being configured to inject the medicament through the needle when the delivery mechanism is activated.

17. The injection device of claim 5, wherein, at the end of dose, the lead screw is rotated such that the radial element extending from the lead screw is aligned with the radial opening of the end of dose mechanism.

18. The injection device of claim 1, further comprising a cartridge containing a medicament to be delivered when the delivery mechanism is activated.

19. The injection device of claim 1, wherein the injection device is an autoinjector.

20. The injection device of claim 1, wherein the radial element is positioned distal to the radial opening of the end of dose mechanism and is operable to pass through the radial opening of the end of dose mechanism such that the radial opening is positioned proximal to the radial opening of the end of dose mechanism when the end of dose mechanism is activated.

* * * * *